United States Patent [19]

Nozaki et al.

[11] Patent Number: 5,447,652
[45] Date of Patent: * Sep. 5, 1995

[54] LIQUID DETERGENT COMPOSITION

[75] Inventors: Toshio Nozaki, Chiba; Takashi Sekiguchi, Yono, both of Japan

[73] Assignee: Kao Corporation, Tokyo, Japan

[ * ] Notice: The portion of the term of this patent subsequent to Mar. 7, 2012 has been disclaimed.

[21] Appl. No.: 94,964

[22] Filed: Jul. 22, 1993

[30] Foreign Application Priority Data

Jul. 22, 1992 [JP] Japan .................. 4-195331

[51] Int. Cl.$^6$ .......................... C11D 7/36; C11D 3/36
[52] U.S. Cl. ................... 252/174.16; 252/135; 252/173; 252/545; 252/546; 252/548; 252/DIG. 5; 252/DIG 13; 252/DIG. 14
[58] Field of Search .................. 252/174.16, 135, 173, 252/545, 546, 548, DIG. 5, DIG. 14, DIG.13

[56] References Cited

U.S. PATENT DOCUMENTS

| | | | |
|---|---|---|---|
| 4,139,485 | 2/1979 | Imokawa et al. | 252/135 |
| 5,062,989 | 11/1991 | Kamegai et al. | 252/174.17 |

FOREIGN PATENT DOCUMENTS

| | | |
|---|---|---|
| 0231997 | 8/1987 | European Pat. Off. . |
| 2027047 | 2/1980 | United Kingdom . |

*Primary Examiner*—P. Achutamurthy
*Attorney, Agent, or Firm*—Oblon, Spivak, McClelland, Maier, & Neustadt

[57] ABSTRACT

A liquid detergent composition which comprises the following components (a), (b) and (c):

(a) at least one compound represented by formula (1):

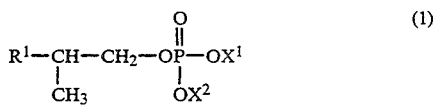

(b) at least one compound represented by formula (2):

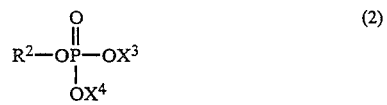

in the proportion by weight falling in the range of $0.2 < (a)/[(a)+(b)] < 1$, and the total amount of (a) and (b) being from 3 to 50% by weight based on the total weight of the composition, and (c) 0.5 to 20% by weight, based on the total weight of the composition, of hydroxysulfobetaine or amidebetaine. The liquid detergent compositions according to the present invention provide excellent feel in use, give no damage to the skin or the hair, produce rich foams, and are stable. Therefore, they are very useful not only as face cleansers, hand cleaners, shampoos and body shampoos, but also as detergents for kitchen use with which the hand skin undergoes contact for a prolonged period of time.

13 Claims, No Drawings

LIQUID DETERGENT COMPOSITION

BACKGROUND OF THE INVENTION

1. Field of the Invention

The present invention relates to liquid detergent compositions, and more particularly, to liquid detergent compositions which are suited for cleansing the skin, hair and the like and which provide excellent feel in use, have excellent foaming ability and are stable for a long term storage.

2. Discussion of the Background

Recently, liquid detergent compositions such as liquid body shampoos have widely been used in place of soap because of their easy handling and good feel in use.

Meanwhile, surfactants of the phosphoric ester type, which are anionic surfactants, are known to be very mild to the skin and the hair, and are utilized as a component of detergent compositions.

When such phosphate surfactants are converted into alkanolamine salts, the resulting Kraft point is low, which results in advantages in the liquidizing process. However, the foaming-forming ability of such alkanolamine salts is poor. On the other hand, when they are converted into an alkali metal salt, it provides rich foams, but the Kraft point is high, which results in a disadvantage in the liquefying process.

Separately, Japanese patent publication Kokai No. 17343/1993 discloses a mixture of phosphate surfactants represented by formulae (1) and (2) shown below as providing rich foams and possessing a low Kraft point.

When these phosphate surfactants are incorporated into a detergent composition, better foam producing ability is obtained than obtainable in the single use of alkanolamine salt, but the property of foam is poor and rough, and besides, foam producing ability is still inferior when compared to other commonly used surfactants in this technical field.

Thus, there remains a need for detergent compositions which have excellent foaming ability and are mild to the skin and are easily prepared.

SUMMARY OF THE INVENTION

Accordingly, it is one object of the present invention to provide novel liquid detergent compositions.

It is another object of the present invention to provide liquid detergent compositions which are mild to the skin.

It is another object of the present invention to provide liquid detergent compositions which have good foaming ability.

It is another object of the present invention to provide liquid detergent compositions which are easily prepared.

These and other objects, which will become apparent during the following detailed description, have been achieved by the inventors' discovery that when a combination of the phosphate surfactants represented by formulae (1) and (2) is further combined with a specified hydroxysulfobetaine, amidebetaine, polyoxyethylene alkyl ether sulfate or its salts, or amidoamino acid or its salts, in a specified proportion, detergent compositions having good foaming ability and providing rich foams can be obtained. The present invention has accomplished based on the above findings.

Accordingly, the present invention provides a liquid detergent composition which comprises the following components (a), (b) and (c):

(a) at least one compound represented by formula (1):

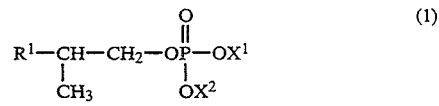

wherein $R^1$ is a linear hydrocarbon group having 5 to 12 carbon atoms, and $X^1$ and $X^2$ independently represent a potassium atom or a hydrogen atom, (b) at least one compound represented by formula (2):

wherein $R^2$ is a linear hydrocarbon group having 11 to 15 carbon atoms, and $X^3$ and $X^4$ independently represent a potassium atom or a hydrogen atom, the amounts by weight of said (a) and (b) being in a relation represented by $0.2<(a)/[(a)+(b)]<1$, and the total amount of (a) and (b) being from 3 to 60% by weight based on the total weight of the composition, and (c) 0.5 to 20% by weight, based on the total weight of the composition, of at least one compound selected from the group consisting of polyoxyethylene alkyl ether sulfate or its salts, amidoamino acid or its salts and compounds of formulae (3) and (4):

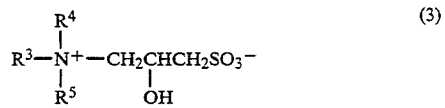

wherein $R^3$ is a saturated or unsaturated hydrocarbon group having 8 to 18 carbon atoms, and $R^4$ and $R^5$ independently represent a methyl group or an ethyl group,

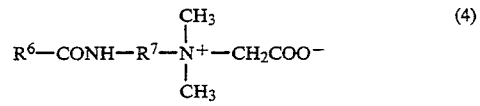

wherein $R^6$ is a saturated or unsaturated hydrocarbon group having 8 to 18 carbon atoms, and $R^7$ represents an ethylene group or a propylene group.

The above and other objects, features and advantages of the present invention will be readily appreciated from the preferred embodiments of the present invention, which will be described subsequently in detail.

DETAILED DESCRIPTION OF THE PREFERRED EMBODIMENTS

Examples of group $R^1$ in formula (1) of component (a) useful in the present invention include linear alkyl or alkenyl groups having 5 to 12 carbon atoms. Among them, linear alkyl groups such as pentyl, hexyl, heptyl, octyl, nonyl, decyl, undecyl and dodecyl are especially preferred.

The liquid detergent compositions of the present invention may further comprise other branched-alkyl phosphates in addition to the methyl-branched-alkyl phosphates of formula (1). Thus, the present liquid detergent compositions may further comprise ethyl-branched-, propyl-branched-, butyl-branched-, and/or pentyl-branched-alkyl phosphates. Such additional branched-alkyl phosphates may be present in amounts so long as no detriment of the good effects of the present compositions is obtained.

Examples of group $R^2$ in formula (2) of component (b) useful in the present invention include alkyl or alkenyl groups having 11 to 15 carbon atoms. Among them, linear alkyl groups such as undecyl, dodecyl, tridecyl, tetradecyl and pentadecyl are especially preferred.

It is preferred that the components (a) and (b) are incorporated into the present composition in such amounts that meet the relation, $0.2 < (a)/[(a)+(b)] < 1$, more preferably, $0.3 < (a)[(a)+(b)] < 0.8$. Proportion of less than 0.2 is not advisable in that the Kraft point of the composition becomes high, which results in disadvantages in obtaining a stable liquid detergent composition.

Salts of phosphoric esters of components (a) and (b) are prepared, for example, by first reacting the corresponding aliphatic alcohol with a phosphorylating agent such as phosphoric anhydride and phosphorus oxychloride, and subsequently neutralizing with potassium hydroxide. As to the aliphatic alcohol, a linear alcohol and a 2-methyl-branched alcohol are used singly or as a mixture to meet the condition, $0.2 < (a)/[(a)+(b)] < 1$. In this connection, commercially obtainable alcohols under Trademarks Diadol 115L (product of Mitsubishi Kasei K.K.) and Dobanol 23I (product of Mitsubishi Yuka K.K.) are examples of a mixture of a linear alcohol and a 2-methyl branched alcohol, and these commercial products are useful for preparing a mixture of the salts of phosphoric esters which meet the mentioned condition, $0.2 < (a)/[(a)+(b)] < 1$.

In the manufacture of the present liquid detergent composition, components (a) and (b) are incorporated in such amounts that the total amount of (a) and (b) falls within the range of from 3 to 50% by weight (hereinafter simply referred to as %), preferably from 10–40% based on the total weight of the composition.

Hydroxysulfobetaine, one of components (c), useful in this invention is represented by the above-mentioned formula (3). In the formula, it is preferred that $R^3$ be C8–18 alkyl or alkenyl and particularly $R^3$ be C8–18 alkyl, with $R^3$ being lauryl or myristyl and $R^4$ and $R^5$ being methyl especially preferred.

Amidebetaine useful in this invention is represented by the above-mentioned formula (4). In the formula, it is preferred that $R^6$ be C7–17 alkyl or alkenyl and particularly $R^6$ be C7–17 alkyl, with $R^6$ being undecyl or tridecyl especially preferred.

Polyoxyethylene alkyl ether sulfate or its salts, one of components (c), useful in this invention are a water-soluble anionic surfactant, and it is preferred to have C11–13 alkyl and be 0° C. and less in the Kraft point.

Amidoamino acid or its salts, one of components (c), useful in this invention are disclosed in U.S. Pat. No. 4,876,034 incorporated herein by reference. The preferable example of such an amidoamino acid or its salts is a secondary or tertiary amidoamino acid or its salts called imidazoline-type surfactant. Among its salts are included salt of alkaline metals such as sodium and potassium, salt of organic amine such as triethanolamine and basic amino acid, and ammonium salt.

Components (c) are one or more compounds selected from the group consisting of these hydroxysulfobetaines, amidebetaines, polyoxyethylne alkyl ether sulfate or its salts, and amidoamino acid or its salts. They are incorporated into the present detergent composition in the range of from 0.5 to 20%, preferably from 1 to 10% based on the total weight of the composition.

It is preferred that the total amount of components (a), (b) and (c) falls within the range of from 4 to 60%, more preferably from 10 to 50% based on the total weight of the composition.

Besides components (a), (b), (c) and water, the liquid detergent composition according to the present invention may contain optional components which are generally contained in ordinary detergent compositions. Examples of such optional components include moisturizers such as propylene glycol, glycerol and sorbitol; viscosity modifiers such as methylcellulose, ethylcellulose, hydroxyethycellulose, carboxyvinyl polymer, xanthan gum, guar gum and ethanol; bacteriostats such as triclosan and triclocarbon; antiinflammatory agents such as dipotassium glycyrrhizate and tocopherol acetate; antidandruff agents such as zinc pyrithione and octopirox, preservatives such as methylparaben and buthylparaben; pearlescent agents; perfumes; colorants; UV absorbers; and antioxidants. These optional components can be used as long as they do not impede the effects of the present invention.

The present liquid detergent composition can be prepared by known methods. It is preferred that the pH of the composition per se fall within the range from 6 to 9.

The liquid detergent composition according to the present invention provide excellent feel in use, do not damage the skin or the hair, produce rich foams, and are stable. Therefore, they are very useful not only as face cleansers, hand cleaners, shampoos and body shampoos, but also as detergents for kitchen use with which the hand skin undergoes contact for a prolonged period of time.

EXAMPLES

The present invention will hereinafter be described more specifically by Example and reference Examples. However, it should be borne in mind that this invention is not limited to and by these examples only.

Reference Example 1

Using various starting alcohols, potassium salts of phosphoric esters (A) and (B) as shown in Table 1 were prepared. The carbon numbers indicated in Table 1 are the total carbon number of the alkyl moiety of the phosphoric ester.

TABLE 1

| Starting alcohol | Mixture of phosphoric esters | | |
|---|---|---|---|
| | Carbon No. of alkyl moiety*[1] | (a)/[(a) + (b)] | Identification |
| Diadol 115L (Mitsubishi Kasei K.K.) | Mixture of 11, 13, 15*[2] | 0.41 | (A) |
| Dobanol 23I (Mitsubishi Yuka | Mixture of 12 and 13*[3] | 0.78 | (B) |

TABLE 1-continued

| Starting alcohol | Mixture of phosphoric esters | | |
|---|---|---|---|
| | Carbon No. of alkyl moiety*1) | (a)/[(a) + (b)] | Identification |
| K.K.) | | | |

*1) In formula (1), $R^1\!-\!CH\!-\!CH_2\!-$
                                          $|$
                                         $CH_3$ In formula (2), $R^2\!-$

*2): Proportion by weight of $C_{11}$, $C_{13}$ and $C_{15}$ is $C_{11}:C_{13}:C_{15} = 47:31:22$. In this mixture, the contents of branched alkyl phosphates are methyl branched (63%), ethyl branched (17%), propyl branched (9%), butyl branched (8%) and pentyl branched (3%).

*3): Proportion by weight of $C_{12}$ and $C_{13}$ is $C_{12}:C_{13} = 43:57$. In this mixture, the contents of branched alkyl phosphates are methyl branched (40%), ethyl branched (16%), propyl branched (15%), butyl branched (19%) and pentyl branched (10%).

Example 1

The liquid detergent compositions as formulated in Tables 2 and 3 were prepared according to a method known per se. They were evaluated with respect to the volume of foam and quality of foam. The results are also shown in Tables 2 and 3.

Evaluation method:
(Volume of foam)

10 fold aqueous solutions were prepared using the liquid detergent compositions, and 100 ml of each solution was placed in a messcylinder (temperatures of solution: 20° C. and 40° C.). Blades were provided in the solution for stirring. The volume (ml) of the foams produced was measured after 30 seconds of stirring. The evaluation was made based on the following standard:

250 ml or more: very good (Rank A)
  200 to 250 ml: good (Rank B)
  200 to 150 ml: slightly insufficient (Rank C)
  less than 150 ml: insufficient (Rank D)

The rotation of the blades was 1000 rpm, and was reversed every 5 seconds.

(Quality of foam)

Ten panelers used each liquid detergent composition for washing their hands. The quality of the foam was evaluated according to the following standard:

5: Very creamy foams
  4: Creamy foams
  3: Ordinary foams
  2: Slightly rough foams
  1: Rough foams

TABLE 2

| Component (%) | Invention products | | | | | |
|---|---|---|---|---|---|---|
| | 1 | 2 | 3 | 4 | 5 | 6 |
| Potassium salt of phosphoric ester (A) | 20 | 30 | 40 | 20 | 20 | 20 |
| Potassium salt of phosphoric ester (B) | — | — | — | — | — | — |
| Lauryldimethylhydroxysulfobetaine | 1 | 5 | 10 | — | 5 | 5 |
| Lauroylamidepropyldimethyl carboxybetaine | — | — | — | 5 | 5 | 10 |
| purified water | balance | | | | | |
| Volume of foam 40° C. | A | A | A | A | A | A |
| 20° C. | A | A | A | A | A | A |
| Quality of foam (Average of 10 panelists) | 3.1 | 3.8 | 4.0 | 3.6 | 4.5 | 4.6 |

TABLE 3

| Component (%) | Invention products | | Comparison products | |
|---|---|---|---|---|
| | 7 | 8 | 1 | 2 |
| Potassium salt of phosphoric ester (A) | — | — | 20 | — |
| Potassium salt of phosphoric ester (B) | 20 | 20 | — | 20 |
| Lauryldimethylhydroxysulfobetaine | 5 | — | — | — |
| Lauroylamidepropyldimethyl carboxybetaine | — | 5 | — | — |
| Purified water | balance | | | |
| Volume of foam 40° C. | A | A | B | B |
| 20° C. | A | A | B | B |
| Quality of foam (Average of 10 panelists) | 3.7 | 3.6 | 2.1 | 1.8 |

| (Formulation) 1 | |
|---|---|
| (1) Potassium salt of phosphoric ester (A) | 30% |
| (2) Lauryldimethylhydroxysulfobetaine | 3 |
| (3) Lauroylamidepropyldimethylcarboxybetaine | 5 |
| (4) Perfume | 0.5 |
| (5) Ethanol | 3 |
| (6) Dibutylhydroxytoluene | 0.1 |
| (7) Water | balance |

(Process)

Components (1) to (3) were dissolved in heated water (7), then cooled down, and subsequently added with components (4) to (6) to prepare a transparent liquid detergent composition (pH 7.5).

| (Formulation) 2 | |
|---|---|
| (1) Potassium salt of phosphoric ester (A) | 30% |
| (2) Sodium salt of amidoamino acid | 7.5 |
| (3) Perfume | 0.5 |
| (4) Ethanol | 3 |
| (5) Dibutylhydroxytoluene | 0.1 |
| (6) Water | balance |

(Process)

Components (1) and (2) were dissolved in heated water (6), then cooled down, and subsequently added with components (3) to (5) to prepare a transparent liquid detergent composition (pH 7.5).

| (Formulation) 3 | |
|---|---|
| (1) Potassium salt of phosphoric ester (A) | 25% |
| (2) Sodium polyoxyethylene (3) lauryl ether sulfate | 5 |
| (3) Perfume | 0.5 |
| (4) Ethanol | 3 |
| (5) Dibutylhydroxytoluene | 0.1 |
| (6) Water | balance |

(Process)

Components (1) and (2) were dissolved in heated water (6), then cooled down, and subsequently added with components (3) to (5) to prepare a transparent liquid detergent composition (pH 7.5).

Twenty monitors washed their faces with the thus obtained detergent composition twice a day, each time for 2 minutes. The monitors found that the detergent produced rich and creamy foams, and they had no complaints such as dry skin.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A liquid detergent composition which comprises the following components (a), (b), and (c):

(a) at least one compound represented by formula (1):

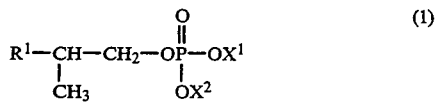

wherein $R^1$ is a linear hydrocarbon group having 5 to 12 carbon atoms, and $X^1$ and $X^2$ independently represent a potassium atom or a hydrogen atom, (b) at least one compound represented by formula (2):

wherein $R^2$ is a linear hydrocarbon group having 11 to 15 carbon atoms, and $X^3$ and $X^4$ independently represent a potassium atom or a hydrogen atom, the amounts by weight of said (a) and (b) being in a relation represented by $0.2 < (a)/[(a)+(b)] < 1$, and the total amount of (a) and (b) being from 3 to 50% by weight based on the total weight of the composition, and (c) 0.5 to 20% by weight, based on the total weight of the composition, of at least one compound selected from the group consisting of compounds of formulae (3) and (4):

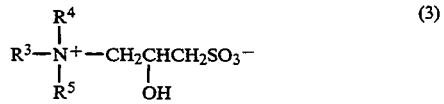

wherein $R^3$ is a saturated or unsaturated hydrocarbon group having 8 to 18 carbon atoms, and $R^4$ and $R^5$ independently represent a methyl group or an ethyl group,

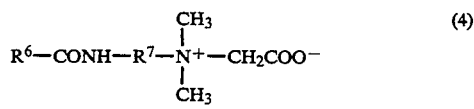

wherein $R^6$ is a saturated or unsaturated hydrocarbon group having 8 to 18 carbon atoms, and $R^7$ represents an ethylene group or a propylene group.

2. The composition as defined in claim 1, wherein component (c) is the hydroxysulfobetaine of formula (3) in which $R^3$ is an alkyl group having 8 to 18 carbon atoms.

3. The composition as defined in claim 1, wherein component (c) is the amidebetaine of formula (4) in which $R^6$ is an alkyl group having 8 to 18 carbon atoms.

4. The composition as defined in claim 1, wherein the total amount of component (a), (b) and (c) falls within the range from 4 to 60% by weight.

5. The composition as defined in claim 1, wherein the total amount of (a) and (b) falls within the range of from 10 to 40% by weight.

6. The composition as defined in claim 1, wherein the amount of (c) falls within the range of from 1 to 10% by weight.

7. The composition as defined in claim 1, wherein the total amount of (a), (b) and (c) falls within the range of from 10 to 50% by weight.

8. The composition as defined in claim 1, wherein (a) and (b) are present in relative amounts which satisfy the relationship $0.3 < (a)/[(a)+(b)] < 0.8$.

9. The composition as defined in claim 1, wherein the total amount of (a) and (b) falls within the range of from 10 to 40% by weight and the amount of (c) falls within the range of from 1 to 10% by weight.

10. The composition as defined in claim 1, wherein the total amount of (a) and (b) falls within the range of from 10 to 40% by weight and (a) and (b) are present in relative amounts which satisfy the relationship $0.3 < (a)/[(a)+(b)] < 0.8$.

11. The composition as defined in claim 1, wherein $R^1$ is a linear hydrocarbon group having 8 to 10 carbon atoms.

12. The composition as defined in claim 1, wherein $R^1$ is an alkyl or alkenyl group, $R^2$ is an alkyl or alkenyl group, $R^3$ is an alkyl or alkenyl group, and $R^6$ is an alkyl or alkenyl group.

13. The composition as defined in claim 1, wherein $R^1$, $R^2$, $R^3$ and $R^6$ are alkyl groups.

* * * * *